(12) United States Patent
Bolli et al.

(10) Patent No.: US 8,715,652 B2
(45) Date of Patent: May 6, 2014

(54) IMMUNOGLOBULIN PREPARATIONS HAVING INCREASED STABILITY

(75) Inventors: Reinhard Bolli, Worb (CH); Gerhard Hodler, Worb (CH); Regula Styger, Bern (CH)

(73) Assignee: CSL Behring AG, Bern (CH)

( * ) Notice: Subject to any disclaimer, the term of this patent is extended or adjusted under 35 U.S.C. 154(b) by 1233 days.

(21) Appl. No.: 10/579,357

(22) PCT Filed: Nov. 17, 2004

(86) PCT No.: PCT/EP2004/013022
§ 371 (c)(1),
(2), (4) Date: May 16, 2006

(87) PCT Pub. No.: WO2005/049078
PCT Pub. Date: Jun. 2, 2005

(65) Prior Publication Data
US 2007/0122402 A1    May 31, 2007

(30) Foreign Application Priority Data
Nov. 18, 2003  (EP) .................................. 03026539

(51) Int. Cl.
A61K 39/395  (2006.01)

(52) U.S. Cl.
USPC ...................................................... 424/130.1

(58) Field of Classification Search
None
See application file for complete search history.

(56) References Cited

U.S. PATENT DOCUMENTS

| | | | |
|---|---|---|---|
| 4,360,451 A | 11/1982 | Schmolka | |
| 4,396,608 A | 8/1983 | Tenold | |
| 4,439,421 A | 3/1984 | Hooper et al. | |
| 4,499,073 A | 2/1985 | Tenold | |
| 4,849,508 A | 7/1989 | Magnin et al. | |
| 4,880,913 A | 11/1989 | Doleschel et al. | |
| 5,164,487 A | 11/1992 | Kothe et al. | |
| 5,177,194 A | 1/1993 | Sarno et al. | |
| 5,593,675 A | 1/1997 | Hodler et al. | |
| 5,871,736 A | 2/1999 | Bruegger et al. | |
| 6,069,236 A | 5/2000 | Burnouf-Radosevich et al. | |
| 6,162,904 A | 12/2000 | Mamidi et al. | |
| 6,171,586 B1 | 1/2001 | Lam et al. | |
| 6,252,055 B1 * | 6/2001 | Relton | 530/414 |
| 6,303,113 B1 | 10/2001 | Woog et al. | |
| 2005/0142139 A1 * | 6/2005 | Schulke et al. | 424/178.1 |

FOREIGN PATENT DOCUMENTS

| | | | |
|---|---|---|---|
| CA | 2 272 245 A1 | 5/1998 | |
| DE | 2 364 792 | 7/1974 | |
| DE | 3 430 320 A1 | 3/1985 | |
| DE | 4 118 912 C1 | 7/1992 | |
| EP | 0 025 275 A1 | 3/1981 | |
| EP | 0 025 275 A2 | 3/1981 | |
| EP | 0 037 078 A2 | 10/1981 | |
| EP | 0 187 712 A2 | 7/1986 | |
| EP | 0 196 761 A2 | 10/1986 | |
| EP | 0 392 717 A1 | 10/1990 | |
| EP | 0 447 585 B1 | 5/1995 | |
| EP | 0 893 450 A1 | 1/1999 | |
| EP | 0 911 037 A1 | 4/1999 | |
| EP | 1 268 551 B1 | 2/2004 | |
| EP | 1 084 147 B1 | 9/2004 | |
| JP | 60-120823 A | 6/1985 | |
| JP | 61-194035 A | 8/1986 | |
| JP | 05-178719 A | 7/1993 | |
| WO | WO 94/29334 | 12/1994 | |
| WO | WO 96/15153 | 5/1996 | |
| WO | WO 98/05686 | 2/1998 | |
| WO | WO 98/28007 | 7/1998 | |
| WO | WO 99/64462 | 12/1999 | |
| WO | WO 02/080976 | 10/2002 | |

OTHER PUBLICATIONS

Andresen, I., et al., "Product Equivalence Study Comparing the Tolerability, Pharmacokinetics, and Pharmachodynamics of Various Human Immunoglobulin-G Formulations," J. Clin Pharmacol, vol. 40, pp. 722-730 (2000).

Kumar, T.K.S., et al., "The Role of Proline in the Prevention of Aggregation During Protein Folding in Vitro," Biochem Mol Biol Int, vol. 46, No. 3, pp. 509-517 (1998).

Shiraki, K., et al. "Biophysical Effect of Amino Acids on the Prevention of Protein Aggregation," J. Biochem., vol. 132, No. 4, pp. 591-595 (2002).

English Language Derwent abstract of JP 05-178719 A, 1993.
English Language Derwent abstract of JP 60-120823 A, 1985.
English Language Derwent abstract of JP 61-194035 A, 1986.

Andersson, I. et al., "An Improved Chromatography Method for Production of IgG From Human Plasma," Presented at XXIII Congress of the International Society of Blood Transfusion (1994).

Azulay, J.-P. et al., "Intravenous Immunoglobulin Treatment in Patients With Motor Neuron Syndromes Associated With Anti-GM$_1$ Antibodies, a Double-Blind, Placebo-Controlled Study," Neurology, vol. 44, pp. 429-432 (1994).

Basta, M. et al., "High-Dose Intravenous Immunoglobulin Exerts its Beneficial Effect in Patients with Dermatomyositis by Blocking Endomysial Deposition of Activated Complement Fragments," The Journal of Clinical Investigation Inc., vol. 94, pp. 1729-1735 (1994).

Berkman, S.A. et al., "Clinical Uses of Intravenous Immunoglobulins," Annals of Internal Medicine, vol. 112, pp. 278-292 (1990).

Biesert L., "Virus Validation Studies of Immunoglobulin Preparations," Clinical and Experimental Rheumatology, vol. 14, Suppl. 15, pp. S47-S52 (1996).

(Continued)

Primary Examiner — Yunsoo Kim
(74) Attorney, Agent, or Firm — Finnegan, Henderson, Farabow, Garrett, & Dunner, L.L.P.

(57) ABSTRACT

The present invention relates to a protein preparation having increased stability, comprising a stabiliser selected from the group consisting of non-polar and basic amino acids and having a pH of 4.0 to 5.2. The invention further relates to a pharmaceutical composition and a method of stabilising protein preparations.

20 Claims, 4 Drawing Sheets

(56) References Cited

OTHER PUBLICATIONS

Bjorkander, J. et al., "1040 Prophylactic Infusions with an Unmodified Intravenous Immunoglobulin Product Causing Few Side-Effects in Patients with Antibody Deficiency Syndromes," Infection vol. 13, No. 3, pp. 102-110 (1985).

Brenner, B., "Clinical Experience With Octagam, A Solvent Detergent (SD) Virus Inactivated Intravenous Gammaglobulin," Clinical and Experimental Rheumatology, vol. 14, Suppl. 15, pp. S115-S119 (1996).

Buckley, R.H. et al., "The Use of Intravenous Immune Globulin in Immunodeficiency Diseases," The New England Journal of Medicine, vol. 325, No. 2, pp. 110-117 (1991).

Cassulis, P. et al., "Ligand Affinity Chromatographic Separation of Serum IgG on Recombinant Protein G-Silica," Clin. Chem., vol. 37, No. 6, pp. 882-886 (1991).

Clerc, M.-F. et al., "Labelling of Colloidal Gold with IgE," Histochemistry, vol. 89, pp. 343-349 (1988).

Cooperative Group for the Study of Immunoglobulin in Chronic Lymphocytic Leukemia, "Intravenous Immunoglobulin for the Prevention of Infection in Chronic Lymphocytic Leukemia, a Randomized, Controlled Clinical Trial," The New England Journal of Medicine, vol. 319, pp. 902-907 (1998).

Dalakas, M.C., "Intravenous Immune Globulin Therapy for Neurologic Diseases, Annals of Internal Medicine," Annals of Internal Medicine, vol. 126, No. 9, pp. 721-730 (1997).

Dwyer, J.M., "Manipulating the Immune System with Immune Globulin," The New England Journal of Medicine, vol. 326, No. 2, pp. 107-116 (1992).

El Alaoui, S. et al., "Development of an Immunocapture Method for Measuring IgA Antibodies to Tissue Transglutaminase in the Sera of Patients with Coeliac Disease," Clinical and Experimental Immunology, vol. 144, pp. 101-109 (2006).

Gammagard S/D, "Humanes Immunoglobulin Zur Intravenosen Anwendung Solvent/Detergent Behandelt," Product Information, Baxter Deutschland GmbH, Edisonstr. 3-4, D-85716 Unterschleibheim, Germany (1994).

Habeeb A.F.S.A. et al., "Preparation of Human Immunoglobulin by Caprylic Acid Precipitation," Preparative Biochemistry, vol. 4, No. 1, pp. 1-17 (1984).

Hansen P. et al., "Isolation and Purification of Immunoglobulins from Chicken Eggs Using Thiophilic Interaction Chromatography," J. Immunological Methods, vol. 215, pp. 1-7 (1998).

Harris, J.R., Ed., "Blood Separation and Plasma Fractionation," pp. 332-333, Wiley-Liss, New York (1991).

Hocini H. et al., "An ELISA Method to Measure Total and Specific Human Secretory IgA Subclasses Based on Selective Degradation by IgA1-Protease," J. Immunological Methods, vol. 235, No. 1-2, pp. 53-60 (2000) (Abstract).

Kaveri, S.-V. et al., "Intravenous Immunoglobulins (IVIg) in the Treatment of Autoimmune Diseases," Clinic Exp. Immunol., vol. 86, pp. 192-198 (1991).

Koopman W.J. et al., "A Sensitive Radioimmunoassay for Quantitation of IgM Rheumatoid Factor," Arthritis and Rheumatism, vol. 23, No. 3, pp. 302-308 (1980).

Lundblad, J.L. et al., "Comparative Studies of Impurities in Intravenous Immunoglobulin Preparations," The University of Chicago, Reviews of Infectious Diseases, vol. 8, Supp. 4, pp. S382-S390 (1986).

McCue, J.P., "Changes in Therapeutic Proteins Caused by Preparation Techniques," Annals of Internal Medicine, vol. 111, No. 4, pp. 271-272 (1989).

Mollnes, T.E. et al., "Effect of Whole and Fractionated Intravenous Immunoglobulin on Complement In Vitro," Molecular Immunology, vol. 34, No. 10, pp. 719-729 (1997).

Nourichafi, N. et al., "Comparison of various chromatographic supports for purifying human plasmatic immunoglobulins from Cohn II + III fraction," Biotechnology of Blood Proteins, vol. 227, pp. 207-212 (1993).

Nydegger, U.E., "Sepsis and Polyspecific Intravenous Immunoglobulins," Jounal of Clinical Apheresis, vol. 12, pp. 93-99 (1997).

Oldham, G. et al., "A Quantitative Method for Measuring in vitro Synthesis of IgA and IgG by Human Rectal Mucosa: Studies on normal controls and patients with hypogammaglobulinaemia," Immunology, vol. 37, pp. 661-668 (1979).

Scopes, R.K., "Protein Purification, Principles and Practice," 2nd Edition, pp. 42-45, published in "Springer Advance Texts in Chemistry," series editor Charles R. Cantor, Springer-Verlag, N.Y. (1987).

Stucki, M. et. al., "Characterisation of a Chromatographically Produced Anti-D Immunoglobulin Product," Journal of Chromatograph B., vol. 700, pp. 241-248 (1997).

Waldo, F.B. et al., "Mixed IgA-IgG Aggregates As a Model of Immune Complexes in IgA Nephropathy," The Journal of Immunology, vol. 142, No. 11, pp. 3841-3846 (1989).

Wang, W., "Antibody Structure, Instability, and Formulation," Journal of Pharmaceutical Sciences, vol. 96, No. 1, pp. 1-26 (2007).

Wells, J.V. et al., "Cord Serum IgA Levels in Australian Infants," J. Paediatrics and Child Health, vol. 16, No. 3, pp. 189-90 (1980) (Abstract).

English Language Derwent abstract of DE 2 364 792, 1974.
English Language Derwent abstract of DE 3 430 320 A1, 1985.
English Language Derwent abstract of DE 4 118 912 C1, 1986.

H. Lilie, "Folding of the Fab fragment within the intact antibody," FEBS Lett. 417: 239-242 (1997).

M.O. Spycher et al., "Well-tolerated liquid intravenous immunoglobulin G preparations (IVIG) have a low immunoglobulin G dimer (IgG-dimer) content," J. Autoimmun. 96 (Suppl. 1): 96 (1996).

R. Bolli et al. "IgG-dimer formation in liquid immunoglobulin preparations is inhibited by nicotinamide and other amphiphilic compounds," J. Autoimmun. 96 (Suppl. 1): 96 (1996).

M. Cramer et al., "Stability over 36 months of a new liquid 10% polyclonal immunoglobulin product (IgPro10, Privigen©) stabilized with L-proline," Vox Sanguinis 96: 219-225 (2009).

G. Lemm, "Composition and properties of IVIg preparations that affect tolerability and therapeutic efficacy," Neurology 59(Suppl. 6): S28-S32 (2002).

W. Wang, "Instability, stabilization, and formulation of liquid protein pharmaceuticals," Int. J. Pharmaceutics 185: 129-188 (1999).

B. Alberts et al., Molecular Biology of the Cell $3^{rd}$ Ed. 1994, cover pages and p. G-12.

A.K. Abbas et al., Cellular and Molecular Immunology $4^{th}$ Ed. 2000, cover pages and pp. 470 and 482.

U.S. Food and Drug Administration package insert for HIZENTRA, Immune Globulin Subcutaneous (Human), 20% Liquid, issued Feb. 2010 (26 pages).

U.S. Food and Drug Administration package insert for PRIVIGEN™, Immune Globulin Intravenous (Human), 10% Liquid, issued Jul. 2007 (20 pages).

International Blood/Plasma News, "CSL BEHRING announced that the U.S. FDA has approved a supplemental Biologics License Application (sBLA) that extends the shelf life of its Privigen 10% liquid intravenous immunoglobulin product from 24 months to 36 months," p. 12, Apr. 2010.

D.L. Tankersley, "Dimer Formation in Immunoglobulin Preparations and Speculations of the Mechanism of Action of Intravenous Immune Globulin in Autoimmune Diseases," Immunological Reviews 139: 159-172 (1994).

CSL Behring press release, "CSL Behring Receives FDA Approval to Extend Shelf Life of Hizentra® from 18 Months to 24 months," Aug. 18, 2010 (2 pages).

* cited by examiner

IMMUNOGLOBULIN PREPARATIONS HAVING INCREASED STABILITY

This application is the National Stage of International Application No. PCT/EP2004/013022 under 35 U.S.C. 371, which claims the benefit of priority to European Patent Application No. 03026539.1, filed Nov. 18, 2003, which is incorporated herein by reference in its entirety.

DESCRIPTION

The present invention relates to a protein preparation having increased stability, comprising a stabiliser selected from the group consisting of non-polar and basic amino acids and having a pH of 4.2 to 5.4. The invention further relates to a pharmaceutical composition and a method of stabilising protein, preparations.

Protein preparations, in particular immunoglobulin preparations for intravenous injection, have been in use for quite some time. Proteins, and immunoglobulin in particular, tend to form aggregates and/or dimers and to fragment or denature. If such solutions are injected intravenously, aggregates can give rise to severe side reactions including anaphylactic shock. In order to avoid aggregation, fragmentation, etc in such protein solutions and to improve their stability, a number of treatments have been tried in the state of the art. For instance, intravenous IgG for clinical use are often lyophilised (freeze-dried) for improved stability on storage, but such preparations must be reconstituted with a diluent before use. The reconstitution step is inconvenient and time consuming and increases the likelihood of contamination of the product. Another way of improving immunoglobulin stability and storage that is well known in the art is the addition of protein-stabilising excipients to the IgG preparation. Known excipients include sugars, polyols, amino acids, amines, salts, polymers and surfactants. Such stabilisation strategies in protein pharmaceuticals are abundant in the art. For example, U.S. Pat. No. 4,499,073 (Tenold) improves the stabilisation through the selection of pH and inonic strength. JP 54020124 discloses the addition of an amino acid to an intramuscular preparation to render it storage stable and safe. JP 57031623 and JP 57128635 disclose the use of arginine and/or lysine with NaCl in 5 to 15% IgG preparations to achieve long-term stability in an intramuscular preparation. JP 56127321 discloses the addition of a sugar alcohol to IgG which works better than the previously used glucose in suppressing aggregation. JP 4346934 discloses the use of low conductivity (less than 1 mmho), pH 5.3 to 5.7 and optionally one or more stabilisers including PEG, human serum albumin and mannitol. U.S. Pat. No. 4,439,421 (Hooper) teaches the addition of a hydrophilic macromolecule, a polyol and another protein to stabilise against ACA (anti-complement activity) generation. U.S. Pat. No. 5,945,098 (Sarno) discloses the stabilisation of isotonic solutions by the addition of amino acids (0.1 to 0.3 M glycine), and non-ionic detergents (polysorbate) and PEG. U.S. Pat. No. 4,186,192 (Lundblad) discloses various additives including amino acids, however, without specifying the use of single specific amino acids. This disclosure includes the stabilisation of IgG with maltose and additionally glycine to 0.1 M. U.S. Pat. No. 4,362,661 (Ono) discloses the use of neutral and basic amino acids to impart stability on a 5% IgG product. All the above mentioned documents disclose IgG preparations of an acidic but still relatively high pH of above 5.2.

In addition to preventing the formation of immunoglobulin aggregates, it has also been recognised that dimer formation, in particular of IgG, can be detrimental to IgG preparations for intravenous use. Although IgG dimers are not known to cause anaphylactic shock, it has nevertheless been found that IgG preparations with a high dimer content are less well tolerated on intravenous injection and can give rise to undesirable side effects including fever, nausea and sometimes lowered blood pressure. Hypotensive side effects have been detected in a rat model by Bleaker et al. (Vox Sanguinis 52, 281-290, 1987), and this also shows an apparent correlation with the dimer content. Dimer formation is less of a problem when an IgG preparation is lyophilised shortly after it is produced. However, if the preparation is intended for storage in non-lyophilised liquid form, dimer concentration increases with storage time.

U.S. Pat. No. 5,871,736 (Bruegger et al.) discloses, immunoglobulin preparations, particularly liquid preparations of IgG for intravenous infusion which comprise one or more amphiphilic stabilisers in order to stabilise against dimer formation. The amphiphilic stabilisers include nicotinic acid and its derivatives, in particular nicotinamide, and, mainly in conjunction with the above, amino acids having uncharged lipophilic side chains, e.g. phenylalanine, methionine, leucine, isoleucine, proline and valine. The experimental disclosure of this prior art document discloses amino acids always in conjunction with nicotinamide, and the concentrations disclosed for the amino acids are 200 mmol/litre for proline, 80 mmol/litre for glycine and: 120 mmol/litre for isoleucine.

The pH range for the preparations disclosed in U.S. Pat. No. 5,871,736 is broadly given as being between 4 and 8, but the actual disclosure of the Examples teaches a pH of 5.3.

Although the above US patent discloses IgG preparations in which dimer formation has been suppressed to a certain degree, it is still desirable to provide protein preparations, in particular immunoglobulin preparations, which show improved stabilisation, in particular at ambient temperature.

The inventors have found that a surprisingly high degree of stabilisation of liquid protein preparations can be achieved by adjusting the pH of the final preparation to between 4.2 and 5.4 and by adding as a stabiliser, a basic or non-polar amino acid.

Thus, the present invention provides a protein preparation having improved stability wherein the preparation comprises one or more stabilisers selected from the group consisting of non-polar and basic amino acids. Exemplary non-polar and basic amino acids, useful for the purposes of the present invention are histidine, arginine, lysine, omithine (basic amino acids) and, isoleucine, valine, methionine, glycine and proline (non-polar amino acids). Particularly useful is proline. The stabiliser may be an amino acid of the group of non-polar or basic amino acids on, its own, or it may be a combination of 2 or more such amino acids. The amino acids are preferably not used in combination with nicotinamide. The amino acid stabilisers may be natural amino acids, amino acid analogues, modified amino acids or amino acid equivalents. L-amino acids are preferred. When proline is used as the stabiliser, it is preferably L-proline. It is also possible to use proline equivalents, e.g. proline analogues.

Surprisingly, it was found that the addition of amino acids on their own, without other stabilisers (such as nicotinamide), and the adjustment of the pH of the final preparation markedly increases the stability of those preparations, particularly at ambient temperature. The increased stability is demonstrated by better stability of the preparations at temperatures between about 2° C. and about 40° C., particularly at ambient temperature which preferably ranges from about 10° C., more preferably from about 15° C., more preferably from about 20° C. to about 30° C., most preferably to about 25° C. The increased stability of the preparations of the invention is also visible at higher temperatures of about 30° C. to about 40° C., including body temperature of about 37° C. Preferably, the increased stability is alternatively or additionally further defined as improved storage time, decreased fragmentation, decreased aggregate formation, decreased dimer formation or/and decreased coloring. The improved storage time means that the preparations of the invention are preferably stable for at least 30 days, preferably at least 60 days, more preferably at least 90 days, more preferably at least 120 days, more preferably even longer than that.

Decreased aggregation preferably means that the preparations show a lower percentage of aggregates (in particular in case of Ig) than conventional preparations. Preferably, the dimer content of the preparations is below, about, 12%, preferably below about 10%, more preferably below about 8%. Decreased colouring preferably means that the optical density of the formulations of the invention is between about 20% and 60% lower than of conventional formulations.

In general, the protein preparations of the present invention are liquid formulations which are useful for intravenous injection. Such preparations can be stored and are stable in liquid form and thus do not require lyophilisation or other treatment and can be readily used.

Preferably, the protein preparation is an immunoglobulin preparation, in particular an antibody preparation wherein the antibodies may be of any idiotype but preferably IgG, IgA or IgM. IgG preparations are particularly preferred. The immunoglobulins can be polyclonal or monoclonal and can be isolated from human or animal blood or produced by other means, for instance by recombinant DNA technology or hybridoma technology. In general, immunoglobulins are obtained from blood plasma by alcohol fractionation, which may be combined with other purification techniques like chromatography, adsorption or precipitation. The immunoglobulins may be treated with trace amounts of enzymes (e.g. pepsin) in order to reduce anti-complementary activity or they may be used whole.

The preparations can be obtained by methods known in the art, except that the pH of the final preparation is adjusted to a relatively high but acidic pH, namely in the range of about pH 4.2 to 5.4. It has been found that this pH range is particularly useful for improving the storage of characteristics of immunoglobulin preparations. The pH range is preferably from 4.5 to about 5.2, a pH range of about 4.6 to 5.0 being particularly preferred, pH 4.8 being especially preferred.

In the course of developing the preparations according to the present invention, it was also found that increasing the final concentration of the stabiliser allows a surprising improvement in the storage characteristics and stability of the preparations. The stabiliser is therefore added to a final concentration of at least 0.2 M. Preferably, the final concentration is between 0.2 M and 0.4 M, more preferably between 0.2 M and 0.3 M, most preferably 0.25 M.

The present invention is particularly useful for protein preparations with a relatively high protein concentration. The final preparation of the present invention has a protein concentration of about 5 to 25% w/v, preferably about 6 to 15% w/v, more preferably about 8 to 12% w/v, most preferably about 10% w/v. The final protein concentration will depend on various factors, such as the administration route, the type of condition to be treated, etc. The skilled person will be able to determine the optimal protein concentration for the intended application. For example, for intravenous infusion, the final preparation of the invention preferably has a protein concentration of about 15 to 20% w/v, preferably about 8 to 12% w/v. In the case of IgG for intravenous use, 10% w/v, i.e. 100 g IgG/litre is particularly useful. For subcutaneous administration a higher dosage may be chosen, for instance about 15 to 20% w/v.

The present invention also provides a pharmaceutical composition comprising the protein preparation of the present invention as well as pharmaceutically acceptable additives. Such additives can be excipients, diluents such as water, and other substances such as non-buffering substances, for example sodium chloride, glycine, sucrose, maltose and sorbitol. Such pharmaceutical compositions may be administered via various routes. For intravenous administration, a dosage of about 0.2 g, preferably, 0.5 g to about 2.0 g of immunoglobulin/kilogram of body weight per day may be used.

A further aspect of the present invention is a method of stabilising protein preparations, in particular immunoglobulin preparations, comprising providing an aqueous protein solution and adding one or more stabilisers selected from the group consisting of basic and non-polar amino acids, wherein the pH of the solution is adjusted to a pH of about 4.2 to 5.4. The pH is preferably adjusted to a value within the preferred ranges given above, pH 4.8 being particularly preferred. The method preferably comprises adjusting the protein concentrations and stabiliser concentrations and choosing the stabiliser or stabilisers as stated above, proline being particularly preferred.

In particular, the method comprises the steps of providing an aqueous protein solution with a protein concentration of about 5 to 25% w/v, adjusting the, pH of the solution to 4.2 to 5.4, and adding one or more stabilisers selected from the group listed above to the solution to give a final stabiliser concentration of 0.2 to 0.4 M to obtain a stable protein preparation. A number of processes are known to isolate immunoglobulins from human plasma or fractions thereof. Immunoglobulins can for example be purified by cold ethanol fractionation and/or octanoic acid fractionation and/or chromatographic procedures. Purification methods that are particularly preferred for the purposes of the present invention include ethanol fractionation, followed by octanoic acid fractionation, followed by low pH treatment, chromatography and nanofiltration. In producing immunoglobulins for intravenous applications such as those for the present invention, special care should preferably be taken to reduce or eliminate immune complexes with anti-complement activity and proteases like kallikrein or plasminogen. The protein to be used in the protein preparations of the present invention is brought to the desired concentration of between about 5 and 25% w/v by known methods, e.g. by ultrafiltration. The pH of the liquid protein preparation is adjusted to a pH of 4.2 to 5.4, and the stabiliser is added to the solution at a final concentration of at least about 0.2 M. Preferably, proline is used as the stabiliser, and it is preferably added at a concentration of about 0.2 M to 0.4 M, preferably about 0.25 M.

The present invention will now be illustrated by means of the following examples and figures.

EXAMPLE 1

Manufacture of a Protein Preparation According to the Invention

The starting material for the intravenous Ig manufacturing process is a licensed intermediate of the Kistler Nitschmann ethanol fractionation process. It is a precipitation of the immunoglobulin fraction from plasma using 19% ethanol at pH 5.8.

High molecular weight proteins, lipoprotein complexes, and other contaminants were precipitated using octanoic acid and were then separated via filtration in the presence of a filter aid. The supernatant was then concentrated before being subjected to a low pH incubation step.

The pH was then adjusted, to pH 6.5 and the material further clarified by filtration to remove precipitated IgA and IgM. The, IgG-enriched solution was then finally purified on an anion exchange resin, according to U.S. Pat. No. 6,093,324, except that the loading was 150 g per litre resin.

Viral elimination was achieved by using a nanofilter.

Formulation: The nanofiltrate was concentrated to 3% protein and diafiltered against 5 volumes of water, followed by concentration of the IgG to 120 g per. litre. Finally, the concentrate was stabilised with 250 mM L-proline, diluted to 100 g IgG per litre and the pH was maintained at pH 4.8. The formulated, bulk was filtered through a 0.2 µm membrane filter.

EXAMPLE 2

Testing of IgG Preparations According to the Invention

IgG concentrate, purified from plasma by a combination of precipitation steps and chromatography and virus inactivated according to Example 1 was split into three portions with 260 ml formulated to pH 4.5, 420 ml formulated to pH 4.8 and 260 ml formulated to pH 5.1. The formulations were then divided, with one half being formulated with 0.25 M glycine and the other with 0.25 M, proline. The final protein concentration was 8% w/v. Aliquots of 10 ml were dispensed in 10 ml Type I glass vials (Type I rubber stoppers).

Figure 1:
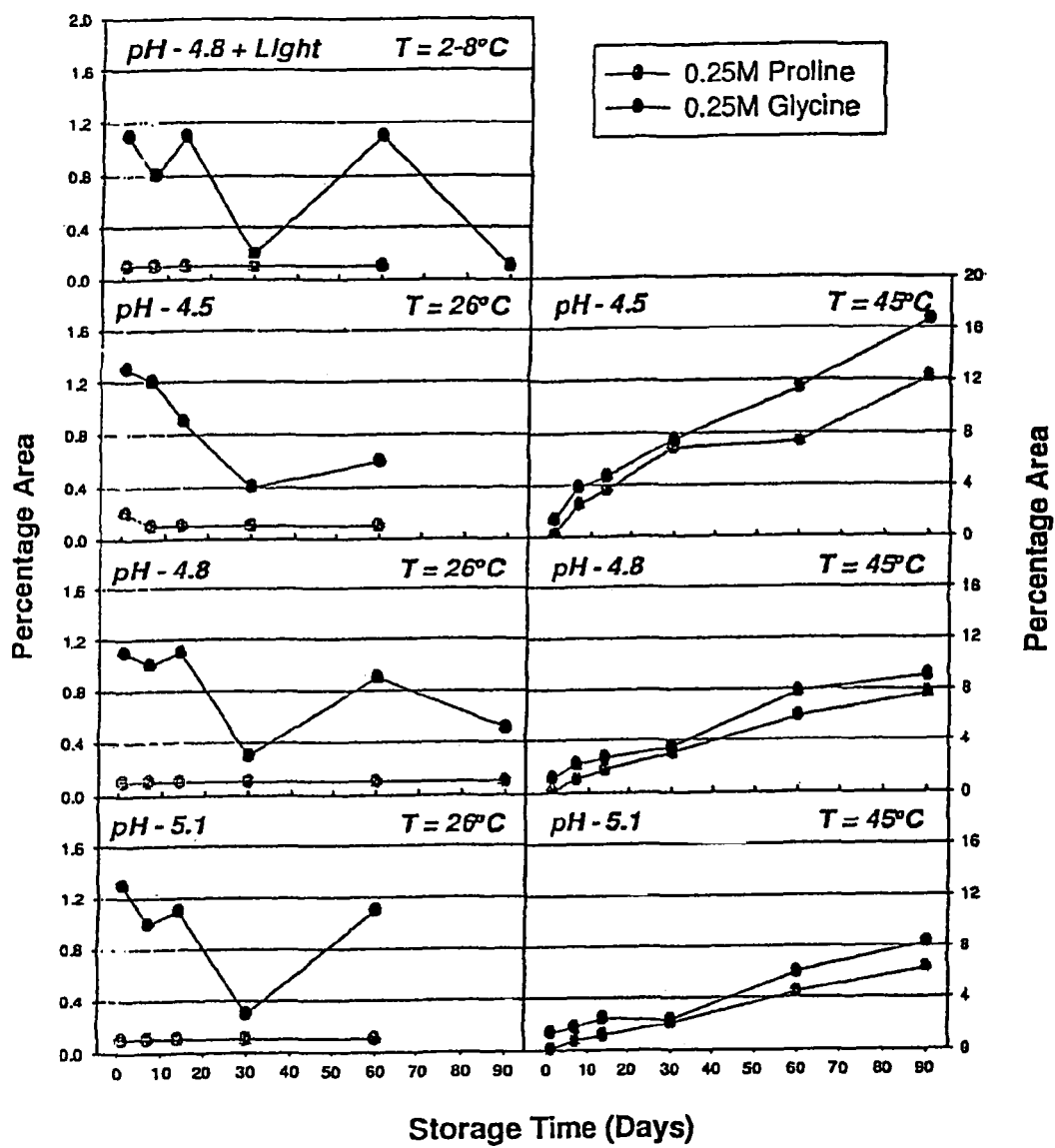
FIG. 1 shows the aggregate content as determined by HPLC for an 8% IgG solution containing either 0.25 M proline or 0.25 M glycine.
Figure 2:
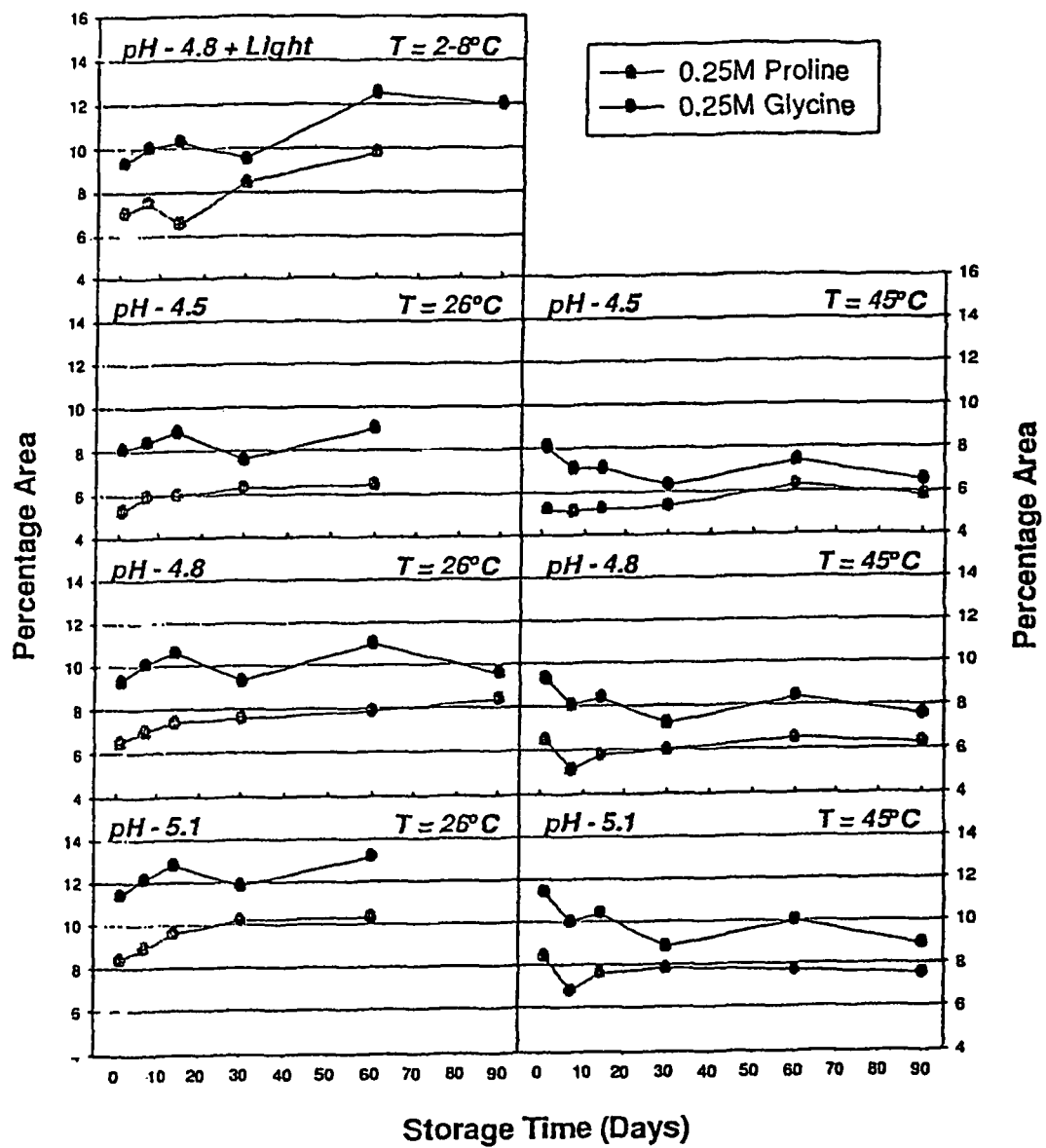
FIG. 2 shows the dimer content as determined by HPLC for an 8% IgG solution containing either 0.25 M proline or 0.25 M glycine.
Figure 3:
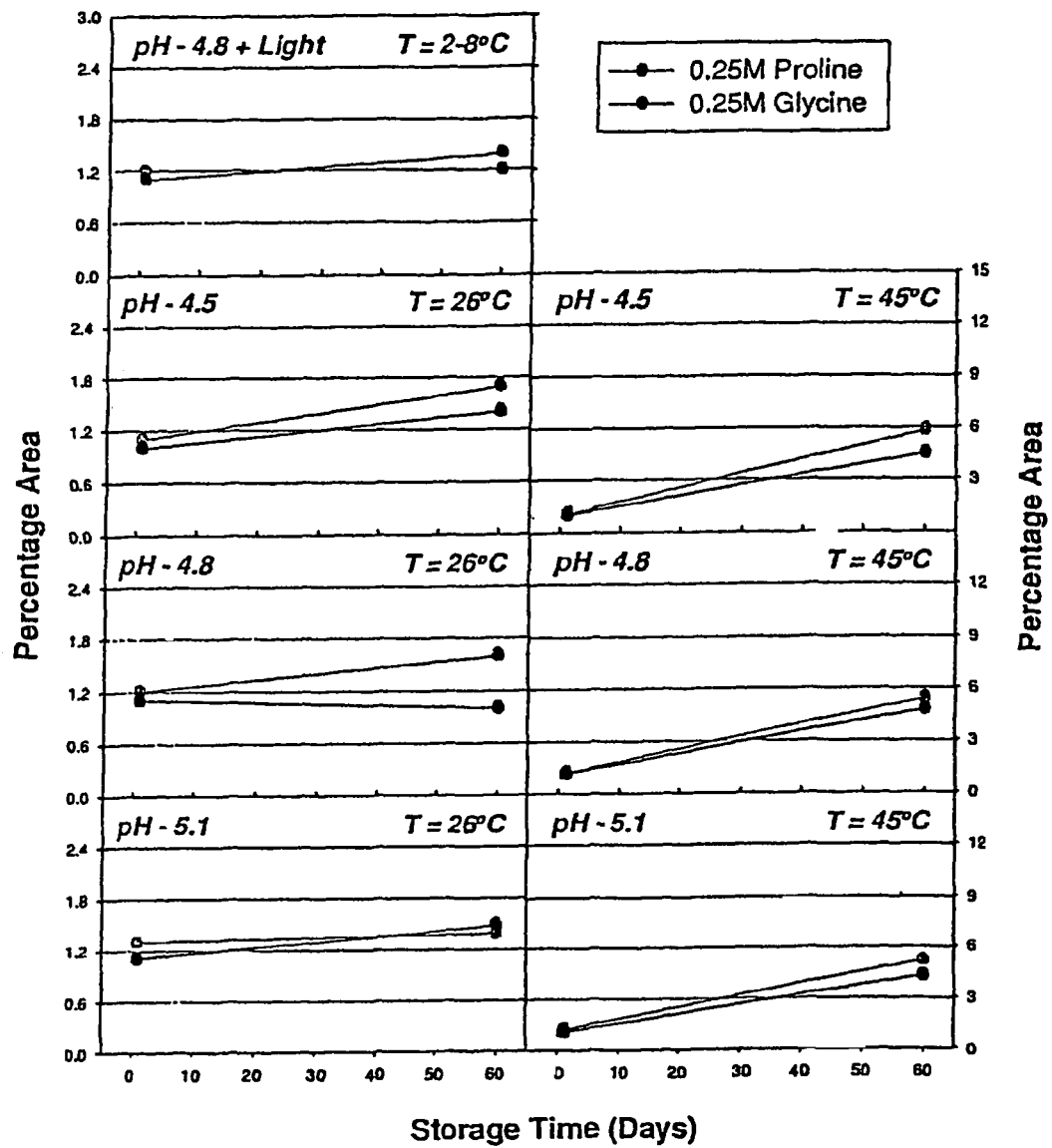
FIG. 3 shows fragment content as determined by SDS PAGE of 8% IgG solutions containing either 0.25 M proline or 0.25 M glycine.
Figure 4:
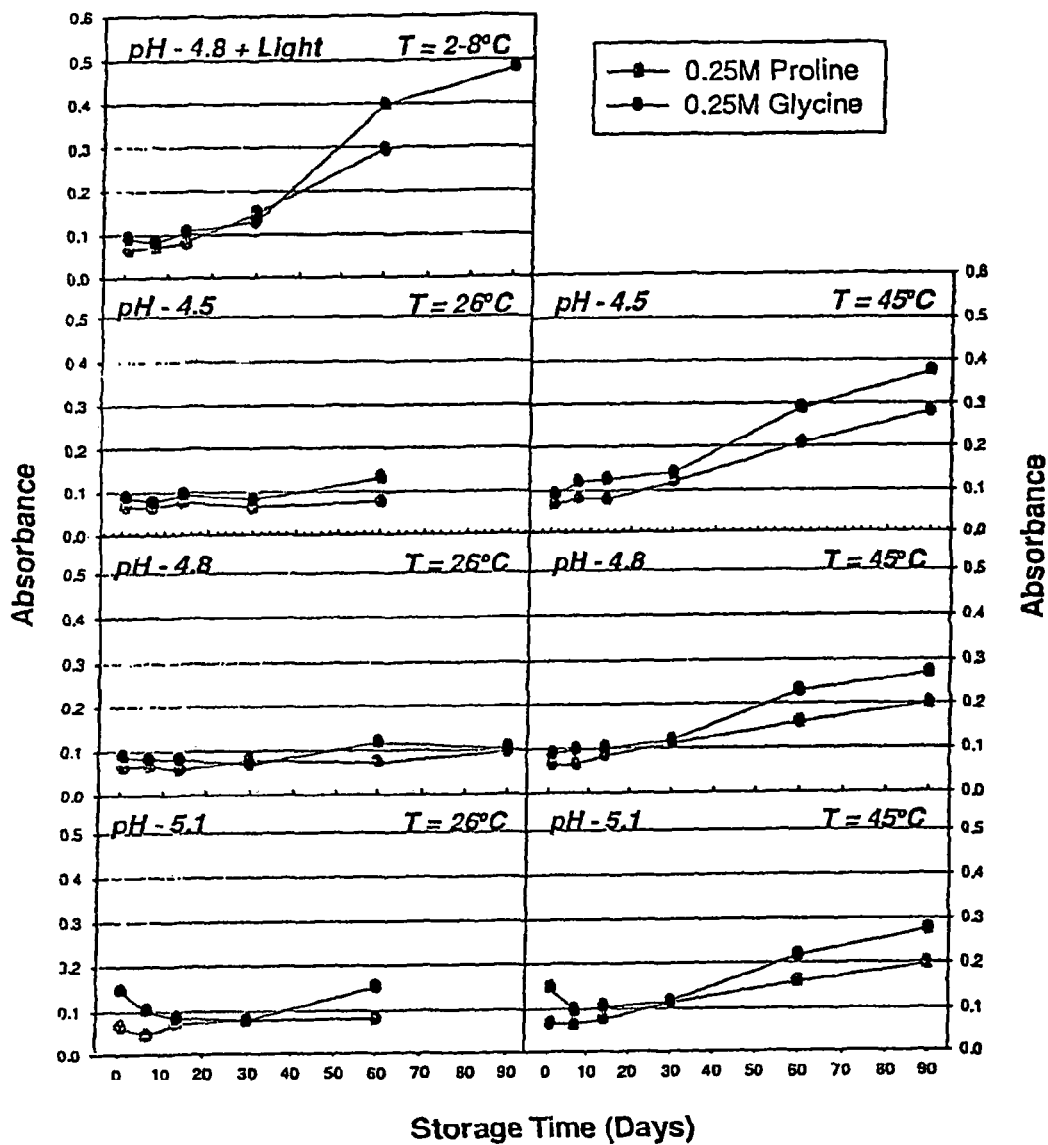
FIG. 4 shows the optical density (UV350-500 nm) of two IgG solutions containing 0.25 M proline or 0.25 M glycine.

The aliquots were stored at three different temperatures, 2-8° C., 26° C. and 45° C. The samples at 2-8° C. were stored in the presence of light (Phillips TLD 18W/33). Samples were incubated at either 26° C. or 45° C. for at least two months in the dark. The results are shown in FIGS. 1 to 4.

Aggregates

The aggregate levels for IgG formulated with glycine were higher than those formulated with proline under all conditions tested.

Significant aggregate formation was promoted by incubation at 45° C. This was similar for both proline and glycine formulations. Lower pH promoted aggregate formation at 45° C., with the pH 4.5 formulations containing 12.2% (proline) and 16.7% (glycine) aggregate at 90 days. In contrast, the pH 5.1 formulations contained 6.3% (proline) and 8.3% (glycine) aggregate at 90 days.

Dimers

The dimer levels were influenced by pH, temperature and excipient type. The pH proved the most important factor, with increased dimer levels observed as the pH of the formulation increased. This was observed for both glycine and proline formulations. The results indicate that formulations containing proline are capable of maintaining lower dimer levels than comparable glycine formulations. The incubation temperature modulates the monomer/dimer equilibrium, with lower temperatures favouring the formation of dimers.

Monomers and Dimers

The combined monomer/dimer content for all formulations at 2-8° C. and 26° C. remained above 90%. Lower levels were observed in IgG solutions formulated with glycine due to their higher aggregate content. Incubation at 45° C. resulted in three formulations having levels below 90% after 60 days (85.1% glycine, pH 4.5, 89.1% proline, pH 4.5 and 89.1% glycine, pH 4.8). Again, these results highlight the increased ability of proline over glycine to preserve the molecular integrity of IgG molecules.

IgG Fragments

The results indicate that the glycine formulations contain slightly lower fragment levels as compared to proline. Incubation temperature and pH proved to be the most important factors influencing IgG fragmentation. At 45° C. the fragment levels for proline formulations range from 5.2% (pH 5.1) to 5.8% (pH 4.5), while the glycine formulations ranged from 4.3% (pH 5.1) to 4.8% (pH 4.8). At elevated pH (4.8-5.1) there was less fragmentation.

Appearance of the Solution

Four main parameters were investigated: clarity, turbidity, particles and visible colouring. Parameters such as appearance, clarity and turbidity were satisfactory. Colouring (yellow/brown) of the solutions occurred during the incubation period and was related to both the incubation temperature and light exposure. The colouring of the IgG formulations was monitored using the optical density test (UV350-500 nm). Increased colour was associated with exposure to light and increased incubation temperatures. The glycine formulations exhibited optical densities that were between 25% and 48% higher than the corresponding proline formulations. These results provide further evidence that proline is a better stabiliser than glycine in IgG solutions. At elevated pH (4.8-5.1) there was less colouration than at lower pH (4.5).

EXAMPLE 3

Stability of IgG Preparations According to the Invention (pH Dependence)

IgG concentrate, purified from plasma by a combination of precipitation steps and chromatography and virus inactivated according to Example 1 was split into two portions and formulated with or without 400 mmol/L L-proline at pH 4.2, 4.8, 5.3 and 6.8. The final protein concentration was 12% w/v. Aliquots of 10 ml were dispensed into glass vials and incubated at 40° C. for at least 3 months in the dark. At time 0 and after 90 days incubation samples were analysed by HPLC for aggregates, dimeric, monomeric IgG, by photometry for absorbance at 350-500 nm, by SDS PAGE (fragments) and specific antibodies directed against hepatitis virus B surface antigen (anti-HBs).

The results presented in Table 1 show that best stability of the IgG solution is obtained at a moderate acidic pH of 4.8 to 5.3.

TABLE 1 pH dependence of the stability of a protein preparation (10%) according to the invention

| | Additive none | | | | | | | |
|---|---|---|---|---|---|---|---|---|
| pH | 4.2 | | 4.8 | | 5.3 | | 6.8 | |
| Incubation time (days) | 0 | 90 | 0 | 90 | 0 | 90 | 0 | 90 |
| Aggregate (%) | 3.5 | 40.2 | 1.16 | 5 | 1.31 | 3.1 | 3.22 | 2.7 |
| Dimer (%) | 6.5 | 3.6 | 10.6 | 11.1 | 12.2 | 13.8 | 16.4 | 19.0 |
| Fragments (%) | 1.4 | 2.6 | 1.3 | 3.5 | 1.3 | 3.6 | 1.5 | 3.4 |
| Absorbance (350–500 nm) | 0.107 | 0.159 | 0.125 | 0.186 | 0.156 | 0.205 | 0.355 | 0.936 |
| anti-HBs (IU/ml) | 7.0 | 2.6 | 6.5 | 3.5 | 6.3 | 3.5 | 6.3 | 3.5 |

| | Additive L-Proline (400 mMol/L) | | | | | | | |
|---|---|---|---|---|---|---|---|---|
| pH | 4.2 | | 4.8 | | 5.3 | | 6.8 | |
| Incubation time (days) | 0 | 90 | 0 | 90 | 0 | 90 | 0 | 90 |
| Aggregate (%) | 1.97 | 26.4 | 0.82 | 4.5 | 0.85 | 2.5 | 1.78 | 2.9 |
| Dimer (%) | 4.3 | 4 | 6.4 | 6.2 | 7.8 | 9.5 | 11.8 | 13.9 |
| Fragments (%) | 1.4 | 2.9 | 1.3 | 3.5 | 1.3 | 4.0 | 1.5 | 3.6 |
| Absorbance (350–500 nm) | 0.202 | 0.234 | 0.134 | 0.213 | 0.125 | 0.235 | 0.249 | 0.55 |
| anti-HBs (IU/ml) | 7.0 | 2.9 | 6.5 | 3.5 | 6.3 | 4.0 | 6.3 | 3.6 |

EXAMPLE 4

Stability of IgG Preparations According to the Invention Formulated with Different Additives IgG concentrates, purified from plasma by a combination of precipitation steps and chromatography and virus inactivated according to Example 1 were formulated with additives of different substance classes (sugars and sugar-alcohols, amino acids, detergents) at pH 4.2, 4.8, 5.3 and 6.8. The final protein concentration was 10% w/v. Aliquots of 10 ml were dispensed into glass vials and incubated at 37° C. or 40° C. for at least 3 months in the dark. After 90 days incubation samples were analysed by HPLC for aggregates, dimeric, monomeric IgG and fragments, by photometry for absorbance at 350-500 nm and by ELISA for specific antibodies directed against hepatitis virus B surface antigen (anti-HBs). The results presented in Table 2 show that best stability of the IgG solution is obtained at a moderate acidic pH of 4.8 or 5.3 with the most favorable formulations with L-proline.

TABLE 2

Stability of a protein preparation (10%) according to the invention formulated with different additives and at different pH.

| Inc. Temp. | Additive | Absorbance 350–500 nm | HPLC Aggregates % | Dimers % | Monomers % | Fragments % | anti-HBs IU/mL |
|---|---|---|---|---|---|---|---|
| pH 4.2 | | | | | | | |
| 37° C. | D(−)Mannit (10%) | 0.134 | 3.00 | 4.19 | 87.37 | 5.44 | 1.63 |
| | Saccharose (10%) | 0.271 | 3.18 | 3.38 | 87.87 | 5.57 | 1.59 |
| | Maltose (10%) | 0.422 | 5.30 | 3.83 | 85.54 | 5.33 | 1.42 |
| | Glycine (250 mmol/L) | 0.177 | 5.82 | 3.75 | 84.64 | 5.79 | 1.57 |
| | L-Proline (250 mmol/L) | 0.166 | 5.50 | 2.98 | 85.87 | 5.64 | 1.70 |
| | Polysorbat 80 (0.02%) | 0.166 | 7.03 | 3.54 | 83.94 | 5.49 | 1.53 |
| | none | 0.172 | 7.83 | 3.67 | 83.11 | 5.39 | 1.52 |
| 40° C. | Glycine (400 mmol/L) | 0.251 | 22.06 | 5.27 | 68.59 | 4.08 | 2.44 |
| | L-Proline (400 mmol/L) | 0.231 | 26.38 | 3.96 | 65.77 | 3.89 | 2.87 |
| | L-Isoleucine (200 mmol/L) | 0.257 | 52.03 | 2.59 | 41.25 | 4.13 | 1.74 |
| | L-Methionine (200 mmol/L) | 0.175 | 37.66 | 3.32 | 55.41 | 3.61 | 2.44 |
| | L-Valine (250 mmol/L) | 0.197 | 29.30 | 4.40 | 62.67 | 3.63 | 2.66 |
| pH 4.8 | | | | | | | |
| 37° C. | D(−)Mannit (10%) | 0.147 | 3.45 | 7.08 | 86.84 | 2.62 | 1.93 |
| | Saccharose (10%) | 0.195 | 0.73 | 6.07 | 90.24 | 2.96 | 1.66 |
| | Maltose (10%) | 0.489 | 0.97 | 7.66 | 88.41 | 2.96 | 1.73 |
| | Glycine (250 mmol/L) | 0.242 | 1.37 | 7.05 | 88.64 | 2.94 | 1.94 |
| | L-Proline (250 mmol/L) | 0.183 | 0.99 | 4.90 | 91.17 | 2.94 | 2.25 |
| | Polysorbat 80 (0.02%) | 0.166 | 1.25 | 7.14 | 88.75 | 2.86 | 1.94 |
| | none | 0.165 | 1.29 | 7.54 | 88.30 | 2.87 | 1.94 |

TABLE 2-continued

Stability of a protein preparation (10%) according to the invention formulated with different additives and at different pH.

| Inc. Temp. | Additive | Absorbance 350–500 nm | HPLC Aggregates % | Dimers % | Monomers % | Fragments % | anti-HBs IU/mL |
|---|---|---|---|---|---|---|---|
| 40° C. | Glycine (400 mmol/L) | 0.241 | 3.79 | 10.42 | 83.47 | 2.32 | 3.77 |
| | L-Proline (400 mmol/L) | 0.213 | 4.47 | 7.09 | 85.96 | 2.48 | 3.54 |
| | L-Isoleucine (200 mmol/L) | 0.488 | 4.88 | 9.67 | 83.27 | 2.18 | 3.87 |
| | L-Methionine (200 mmol/L) | 0.174 | 5.93 | 7.46 | 84.08 | 2.53 | 3.83 |
| | L-Valine (250 mmol/L) | 0.207 | 6.48 | 9.58 | 81.53 | 2.41 | 3.71 |
| pH 5.3 | | | | | | | |
| 37° C. | D(−)Mannit (10%) | 0.179 | 1.39 | 10.49 | 85.62 | 2.50 | 1.84 |
| | Saccharose (10%) | 0.185 | 0.61 | 8.46 | 88.36 | 2.57 | 1.88 |
| | Maltose (10%) | 0.516 | 0.76 | 11.04 | 85.51 | 2.69 | 1.70 |
| | Glycine (250 mmol/L) | 0.263 | 0.98 | 9.09 | 87.59 | 2.34 | 1.92 |
| | L-Proline (250 mmol/L) | 0.195 | 0.78 | 7.34 | 89.58 | 2.30 | 2.20 |
| | Polysorbat 80 (0.02%) | 0.196 | 0.94 | 9.56 | 86.94 | 2.56 | 1.91 |
| | none | 0.177 | 0.93 | 10.13 | 86.40 | 2.53 | 1.90 |
| 40° C. | Glycine (400 mmol/L) | 0.336 | 2.82 | 12.75 | 82.43 | 2.00 | 3.92 |
| | L-Proline (400 mmol/L) | 0.235 | 2.49 | 9.54 | 85.90 | 2.07 | 4.02 |
| | L-Isoleucine (200 mmol/L) | 0.275 | 4.14 | 11.06 | 82.76 | 2.04 | 3.73 |
| | L-Methionine (200 mmol/L) | 0.207 | 3.21 | 9.67 | 84.42 | 2.71 | 3.58 |
| | L-Valine (250 mmol/L) | 0.253 | 4.26 | 12.00 | 81.30 | 2.44 | 3.93 |
| pH 6.8 | | | | | | | |
| 37° C. | D(−)Mannit (10%) | 0.300 | 4.94 | 12.14 | 80.25 | 2.67 | 1.61 |
| | Saccharose (10%) | 0.270 | 0.95 | 12.19 | 84.16 | 2.70 | 1.89 |
| | Maltose (10%) | 1.008 | 5.96 | 16.81 | 74.46 | 2.77 | 1.34 |
| | Glycine (250 mmol/L) | 0.807 | 1.19 | 12.34 | 84.39 | 2.08 | 1.87 |
| | L-Proline (250 mmol/L) | 0.328 | 1.10 | 10.89 | 85.87 | 2.14 | 1.90 |
| | Polysorbat 80 (0.02%) | 0.308 | 1.50 | 13.85 | 81.74 | 2.92 | 1.60 |
| | none | 0.344 | 1.40 | 13.68 | 81.91 | 3.00 | 1.73 |
| 40° C. | Glycine (400 mmol/L) | 1.063 | 3.00 | 16.61 | 78.08 | 2.32 | 3.72 |
| | L-Proline (400 mmol/L) | 0.550 | 2.89 | 13.95 | 80.69 | 2.47 | 3.61 |
| | L-Isoleucine (200 mmol/L) | 0.840 | 4.47 | 15.38 | 77.77 | 2.38 | 3.87 |
| | L-Methionine (200 mmol/L) | 0.687 | 2.96 | 13.68 | 79.79 | 3.57 | 3.66 |
| | L-Valine (250 mmol/L) | 1.083 | 4.62 | 15.16 | 75.33 | 4.89 | 3.13 |

The invention claimed is:

1. A stable polyclonal IgG preparation, wherein the preparation comprises polyclonal IqG and a stabilizer comprising proline, has a pH of about 4.2 to about 5.4, and does not comprise nicotinamide.

2. The preparation of claim 1, wherein the concentration of IgG in the preparation is 8-12% w/v.

3. The preparation of claim 2, wherein the concentration of IgG in the preparation is 10% w/v.

4. The preparation of claim 1, wherein said preparation has a pH of about 4.6 to about 5.0.

5. The preparation of claim 1, wherein said proline is L-proline, and the concentration of L-proline in the preparation is from 0.2 to 0.3 M.

6. The preparation of claim 1, wherein the preparation is a liquid preparation that has not been lyophilized and is not lyophilized prior to administration.

7. The preparation of claim 1, wherein the proline is L-proline and the concentration of the L-proline in the preparation is from 0.2 to 0.4 M, and wherein the concentration of IgG in the preparation is 6-15% w/v.

8. The preparation of claim 7, wherein the preparation is a liquid preparation that has not been lyophilized and is not lyophilized prior to administration.

9. The preparation of claim 1, wherein the preparation has a pH of about 4.6 to about 5.0, the proline is L-proline and the concentration of the L-proline in the preparation is from 0.2 to 0.3 M, and wherein the concentration of IgG in the preparation is 8-12% w/v.

10. The preparation of claim 9, wherein the preparation is a liquid preparation that has not been lyophilized and is not lyophilized prior to administration.

11. The polyclonal IqG preparation of claim 1 wherein the proline is L-proline and the concentration of the L-proline in the preparation is from 0.2 to 0.4 M, and wherein the concentration of IgG in the preparation is 15-20% w/v.

12. The preparation of claim 11, wherein the preparation is a liquid preparation that has not been lyophilized and is not lyophilized prior to administration.

13. A stable liquid polyclonal IgG preparation, wherein the preparation comprises polyclonal IgG and a stabilizer consisting essentially of proline, wherein the preparation has a pH of about 4.2 to about 5.4, and wherein the preparation is not lyophilized prior to administration.

14. The stable liquid polyclonal IgG preparation of claim 13, wherein the proline is L-proline and the concentration of the L-proline in the preparation is from 0.2 to 0.4 M, and wherein the concentration of IgG in the preparation is 6-15% w/v.

15. The stable liquid polyclonal IgG preparation of claim 13, wherein the proline is L-proline and the concentration of the L-proline in the preparation is from 0.2 to 0.3 M, and wherein the concentration of IgG in the preparation is 8-12% w/v.

16. The stable liquid polyclonal IgG preparation of claim 13, wherein the proline is L-proline and the concentration of the L-proline in the preparation is from 0.2 to 0.4 M, and wherein the concentration of IgG in the preparation is 15-20% w/v.

17. The preparation of claim 11, wherein the concentration of IgG in the preparation is 20% w/v.

18. A method of preparing the preparation of claim 1, comprising providing an aqueous polyclonal IgG solution, adding proline, and adjusting the pH to a pH from about 4.2 to about 5.4.

19. The method of claim 18, wherein the pH is adjusted to 4.8.

20. The method of claim 18, wherein the final concentration of the proline in the preparation is from 0.2 to 0.4 M.

* * * * *